(12) United States Patent
Johansen

(10) Patent No.: US 7,503,217 B2
(45) Date of Patent: Mar. 17, 2009

(54) SONAR SAND DETECTION

(75) Inventor: Espen S. Johansen, Houston, TX (US)

(73) Assignee: Weatherford/Lamb, Inc., Houston, TX (US)

( * ) Notice: Subject to any disclaimer, the term of this patent is extended or adjusted under 35 U.S.C. 154(b) by 442 days.

(21) Appl. No.: 11/341,167

(22) Filed: Jan. 27, 2006

(65) Prior Publication Data

US 2007/0175280 A1 Aug. 2, 2007

(51) Int. Cl.
G01H 3/12 (2006.01)
G01N 24/00 (2006.01)

(52) U.S. Cl. .......................... 73/599; 73/61.75; 73/799
(58) Field of Classification Search .................. 73/599, 73/799, 61.75
See application file for complete search history.

(56) References Cited

U.S. PATENT DOCUMENTS

| | | | |
|---|---|---|---|
| 3,149,492 A | 9/1964 | Weinberg | |
| 3,851,521 A | 12/1974 | Ottenstein | |
| 4,080,837 A | 3/1978 | Alexander | |
| 4,114,439 A | 9/1978 | Fick | |
| 4,144,768 A | 3/1979 | Anderson | |
| 4,159,646 A | 7/1979 | Paulsen | |
| 4,164,865 A | 8/1979 | Hall | |
| 4,236,406 A | 12/1980 | Reed | |
| 4,275,602 A | 6/1981 | Fujishiro | |
| 4,445,389 A | 5/1984 | Potzick | |
| 4,499,418 A | 2/1985 | Helms | |
| 4,515,473 A | 5/1985 | Mermelstein | |
| 4,520,320 A | 5/1985 | Potzick | |
| 4,546,649 A | 10/1985 | Kantor | |
| 4,706,501 A | 11/1987 | Atkinson | |
| 4,788,852 A | 12/1988 | Martin | |
| 4,813,270 A | 3/1989 | Baillie | |
| 4,862,650 A | 9/1989 | Nice | |
| 4,864,868 A | 9/1989 | Khalifa | |
| 4,884,457 A | 12/1989 | Hatton | |
| 4,896,540 A | 1/1990 | Shakkottai | |
| 4,932,262 A | 6/1990 | Wlodarczyk | |
| 4,947,127 A | 8/1990 | Helms | |
| 4,950,883 A | 8/1990 | Glenn | |
| 4,976,151 A | 12/1990 | Morishita | |
| 4,996,419 A | 2/1991 | Morey | |

(Continued)

FOREIGN PATENT DOCUMENTS

DE 19511234 12/1995

(Continued)

OTHER PUBLICATIONS

GB Search Report, Application No. 0700533.3, Dated May 2, 2007.

Primary Examiner—Hezron Williams
Assistant Examiner—Samir M Shah
(74) Attorney, Agent, or Firm—Patterson & Sheridan, L.L.P.

(57) ABSTRACT

Methods and apparatus for detecting particles flowing in a fluid within a conduit involve analysis of acoustic pressure signals detected with an array of at least two pressure sensors. The analysis can include monitoring for attenuation in power of the acoustic disturbances within the fluid and/or a reduction in a speed of sound in the fluid. This attenuation in power or reduction in the speed of sound can be detected to provide an output or otherwise indicate that particles are present in the fluid.

20 Claims, 9 Drawing Sheets

U.S. PATENT DOCUMENTS

| | | |
|---|---|---|
| 5,024,099 A | 6/1991 | Lee |
| 5,031,460 A | 7/1991 | Kanenobu |
| 5,040,415 A | 8/1991 | Barkhoudarian |
| 5,051,922 A | 9/1991 | Toral |
| 5,058,437 A | 10/1991 | Chaumont |
| 5,083,452 A | 1/1992 | Hope |
| 5,099,697 A | 3/1992 | Agar |
| 5,115,670 A | 5/1992 | Shen |
| 5,152,181 A | 10/1992 | Lew |
| 5,207,107 A | 5/1993 | Wolf |
| 5,218,197 A | 6/1993 | Carroll |
| 5,317,576 A | 5/1994 | Leonberger |
| 5,321,991 A | 6/1994 | Kalotay |
| 5,347,873 A | 9/1994 | Vander Heyden |
| 5,361,130 A | 11/1994 | Kersey |
| 5,363,342 A | 11/1994 | Layton |
| 5,367,911 A | 11/1994 | Jewell |
| 5,372,046 A | 12/1994 | Kleven |
| 5,398,542 A | 3/1995 | Vasbinder |
| 5,401,956 A | 3/1995 | Dunphy |
| 5,426,297 A | 6/1995 | Dunphy |
| 5,440,932 A | 8/1995 | Wareham |
| 5,493,390 A | 2/1996 | Varasi |
| 5,493,512 A | 2/1996 | Puebe |
| 5,513,913 A | 5/1996 | Ball |
| 5,564,832 A | 10/1996 | Ball |
| 5,576,497 A | 11/1996 | Vignos |
| 5,591,922 A | 1/1997 | Segeral |
| 5,597,961 A | 1/1997 | Marreli |
| 5,639,667 A | 6/1997 | Heslot |
| 5,642,098 A | 6/1997 | Santa Maria |
| 5,644,093 A | 7/1997 | Wright |
| 5,654,551 A | 8/1997 | Watt |
| 5,670,529 A | 9/1997 | Clarke |
| 5,680,489 A | 10/1997 | Kersey |
| 5,689,540 A | 11/1997 | Stephenson |
| 5,708,211 A | 1/1998 | Jepson |
| 5,730,219 A | 3/1998 | Tubel |
| 5,732,776 A | 3/1998 | Tubel |
| 5,741,980 A | 4/1998 | Hill |
| 5,803,167 A | 9/1998 | Bussear |
| 5,804,713 A | 9/1998 | Kluth |
| 5,842,347 A | 12/1998 | Kinder |
| 5,845,033 A | 12/1998 | Berthold |
| 5,906,238 A | 5/1999 | Carmody |
| 5,907,104 A | 5/1999 | Cage |
| 5,908,990 A | 6/1999 | Cummings |
| 5,925,821 A | 7/1999 | Bousquet |
| 5,925,879 A | 7/1999 | Hay |
| 5,939,643 A | 8/1999 | Oertel |
| 5,956,132 A | 9/1999 | Donzier |
| 5,959,547 A | 9/1999 | Tubel |
| 5,963,880 A | 10/1999 | Smith |
| 5,975,204 A | 11/1999 | Tubel |
| 5,992,519 A | 11/1999 | Ramakrishnan |
| 5,996,690 A | 12/1999 | Shaw |
| 6,002,985 A | 12/1999 | Stephenson |
| 6,003,383 A | 12/1999 | Zielinska |
| 6,003,385 A | 12/1999 | De Vannssay |
| 6,009,216 A | 12/1999 | Pruett |
| 6,016,702 A | 1/2000 | Maron |
| 6,158,288 A | 12/2000 | Smith |
| 6,216,532 B1 | 4/2001 | Stephenson |
| 6,233,374 B1 | 5/2001 | Ogle |
| 6,279,660 B1 | 8/2001 | Hay |
| 6,354,147 B1 | 3/2002 | Gysling |
| 6,378,357 B1 | 4/2002 | Han et al. |
| 6,748,811 B1 | 6/2004 | Iwanga et al. |
| 6,837,098 B2 | 1/2005 | Gysling |
| 2005/0171710 A1* | 8/2005 | Gysling et al. ............... 702/54 |

FOREIGN PATENT DOCUMENTS

| | | |
|---|---|---|
| EP | 0684458 | 5/1995 |
| FR | 2357868 | 7/1976 |
| GB | 2399637 | 9/2004 |
| JP | 406082281 | 9/1992 |
| WO | WO 93/14382 | 7/1993 |
| WO | WO 96/04528 | 2/1996 |
| WO | WO 00/00793 | 1/2000 |
| WO | WO 2004/044532 | 5/2004 |

* cited by examiner

SONAR SAND DETECTION

BACKGROUND OF THE INVENTION

1. Field of the Invention

Embodiments of the invention generally relate to detecting particles flowing in a fluid within a conduit.

2. Description of the Related Art

Production of particles, such as sand, concerns operators of oil/gas wells because of possible catastrophic consequences on production. In this disclosure, "sand" refers to solid particulate matter as would be found in an oil/gas well, without particular regard to its size or diameter. The production of sand may result in clogged well lines that can effectively fill in the well and halt production. Sand can also congest separator tanks, which typically connect other producing wells. When this congestion occurs, the production of all oil wells feeding into the separator tanks must be halted. Furthermore, sand production can erode flow lines, chokes, etc., and can cause a catastrophic failure or breach of the piping system.

Mechanical sand control devices such as expandable sand screens, gravel packs, etc. are designed to mitigate sand production. However, operators still need to monitor sand, so that evasive action can be taken if sand production is increasing beyond tolerable levels, due to e.g., sand screen failure. Once sand is detected, the operator may lower the drawdown to reduce the amount of produced sand. Operators often apply conservative production limits for the maximum production rates due to the serious consequences associated with undetected sand production. Thus, a large incentive exists in the industry for methods of detecting sand quickly and continuously.

A variety of methods currently exist in the oil and gas industry to detect sand production. One such method involves physically filtering a sample of produced fluids to check for solid particles. However, contamination of the separator tanks and completion equipment may occur prior to the filtering that takes place after the fluid has risen to the top of the well. Furthermore, the filtering of selected samples only detects sand at designated time intervals.

Intrusive sand erosion probes provide an alternative technology to detect sand. The probe includes a sacrificial element immersed in the flow stream. Measured changes in electrical properties as the element erodes from impinging sand particles can be used to detect sand. Disadvantages of the probe include a limited lifespan and the fact that the element must enter the pipe and obstruct part of the flow stream. Accordingly, the probe is unsuitable for downhole installation.

Another device that continuously monitors for sand production senses the vibrations caused by sand impacting the pipe in which the sand flows. The device clamps on to the pipe at a ninety degree elbow or section of the pipe where the fluid takes an abrupt turn. Consequently, the devise is unsuitable in straight or slightly bent piping networks downhole and is thereby limited to the surface environment. This technique of listening for impact vibration of the sand often requires in situ calibration by artificial injection of sand into the flow stream and can still provide false readings if the multiphase flow field is changing.

Fiber optic sensors and flowmeters already monitor parameters such as fluid sound speed, fluid velocity, pressure, and temperature. Such fiber optic based flowmeters are disclosed in the following U.S. Patents, and are hereby incorporated by reference in their entireties: U.S. Pat. No. 6,782,150, entitled "Apparatus for Sensing Fluid in a Pipe;" U.S. Pat. No. 6,691,584, entitled "Flow Rate Measurements Using Unsteady Pressures;" and U.S. Pat. No. 6,354,147, entitled "Fluid Parameter Measurement in Pipes Using Acoustic Pressures," hereinafter referred to as the "flowmeter references." However, these flowmeter references fail to provide any ability to reliably monitor sand production at the surface or downhole in real-time while other parameters are measured.

Therefore, there exists a need for a sensor that can be placed at any location along a production pipe to detect sand particles within fluid flow.

SUMMARY OF THE INVENTION

Embodiments of the invention generally relate to detecting particles flowing in a fluid within a conduit. The conduit can be a production pipe in a wellbore. An array of at least two pressure sensors disposed anywhere along the production pipe detect acoustic pressure signals that enable analysis for detection of sand flowing within the production pipe.

According to one embodiment, a method of detecting particles in a fluid within a conduit includes measuring acoustic disturbances within the fluid with at least two pressure sensors in order to produce a pressure signal data set, and monitoring the data set to detect a predefined change relative to a control set, wherein the change indicates that particles are present in the fluid and is selected from at least one of a reduction in power of the acoustic disturbances within the fluid relative to the control set and a reduction in a speed of sound in the fluid relative to the control set.

In a further embodiment, a system for detecting particles in a fluid within a conduit includes at least two sensors for detecting acoustic disturbances within the fluid and disposed along the conduit, a processor for converting pressure signals from the at least two sensors into a data set indicative of power of the acoustic disturbances, an analyzer for assessing the data set and determining whether the power of the acoustic disturbances is attenuated relative to a control set, and an output to indicate presence of particles in the fluid when the data set is attenuated relative to the control set.

For yet another embodiment, a method of detecting particles in a fluid within a conduit includes measuring acoustic disturbances within the fluid with at least two pressure sensors to produce pressure signals, converting the pressure signals to provide a data set indicative of power of the acoustic disturbances, assessing the data set and determining whether the power of the acoustic disturbances is attenuated relative to a control set, and determining if particles are in the fluid based on whether the data set is attenuated relative to the control set indicating that particles are present.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

For some embodiments of the invention, a phased spatial array of optical sensors with Bragg gratings measure acoustic pressure waves propagating through the fluid. The sensors may measure the acoustic pressure waves by techniques disclosed in U.S. Pat. No. 6,354,147 entitled, "Fluid Parameter Measurement In Pipes Using Acoustic Pressures," or by sonar processing techniques disclosed in U.S. Pat. No. 6,587,798 entitled, "Method And System For Determining The Speed Of Sound In A Fluid Within A Conduit," both of which are incorporated herein by reference in their entirety. Furthermore, the optical sensors may comprise the acoustic sensing arrays found in the incorporated "flowmeter references" listed above. Analyzing the power of the signals provided by the optical sensors enables determination of the presence of particles, such as sand, within the fluid.

Acoustic "background" noise is present within the fluid flowing within the production pipe. These acoustics arise from a variety of sources and can be useful in detection of particles in the fluid. For example, naturally occurring acoustic noise in the flowing fluid or fluid mixture can be used to determine the presence of particles flowing within the fluid.

Figure 1:
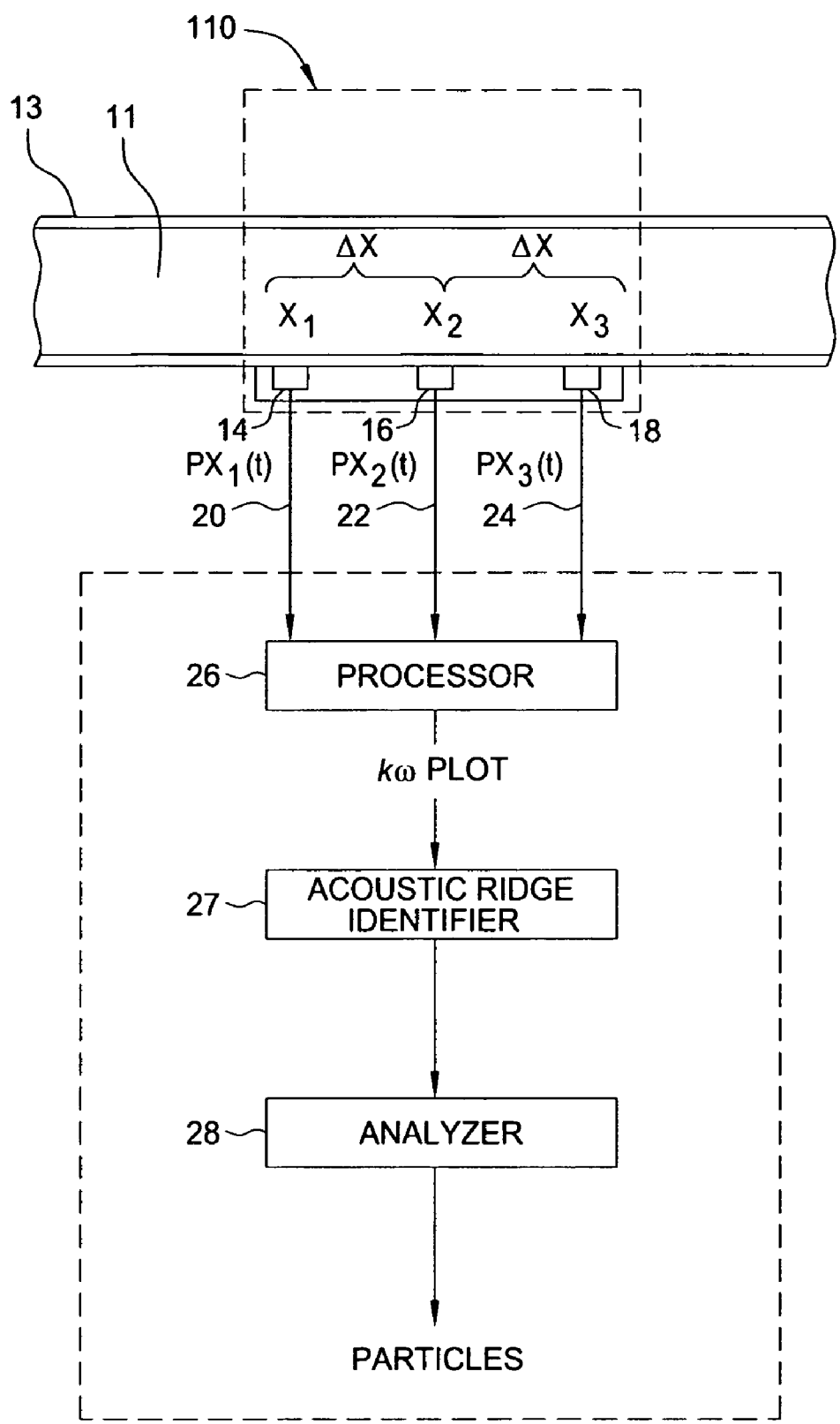
FIG. 1 illustrates a system for detecting the presence of particles in a fluid, according to one embodiment of the invention.

FIG. 1 shows a system according to one embodiment of the invention for detecting particles in a fluid 11 flowing within a conduit 13. An array of pressure sensors 14, 16, 18 provides signals 20, 22, 24 indicative of the fluid pressure at each sensor location at a number of successive instants of time. Additional sensors or only two sensors can also be used for some embodiments. The array of sensors 14, 16, 18 measures the unsteady pressure disturbances within the fluid 11 caused by sand and other phenomenon propagating with or within the fluid. The sensors 14, 16, 18 may include fiber optic sensors that may coil around the conduit 13 in a series of wraps. As disclosed in the incorporated "flowmeter references," each wrap may be separated by a single Bragg grating for time division multiplexing (TDM) or each wrap may be separated by a pair of Bragg gratings for wavelength division multiplexing (WDM). Other types of pressure sensors, such as electrical, piezofilm, polyvinylidene fluoride (PVDF), or mechanical sensors, can be used and are disclosed in the "flowmeter references."

The sensors 14, 16, 18 produce time varying pressure ($Px_i$(t)) signals indicative of the pressure of the acoustic disturbance detected at each of the sensors, rendering information about pressure as a function of both location (x) and time (t), i.e., P(x,t). For some embodiments, these pressure signals are converted at a processor 26 into a kω plot, where k is wavenumber ($2\pi/\lambda$), and ω is the angular frequency ($2\pi f$). This conversion is affected at the processor 26 and can involve the use of Fourier Transform algorithms. Other spatial/temporal conversions (e.g., a xω plot, a kt plot, etc.) are also possible such that the "kω plot" includes these other types of spatial/temporal conversions. A two-dimensional transform is utilized since two variables (x and t) are transformed into two different variables (ω and k). Details of the foregoing conversions, physics of wave propagation inside a pipe containing a fluid, and other relevant considerations are disclosed in previously incorporated U.S. Pat. No. 6,587,798.

Figure 2:
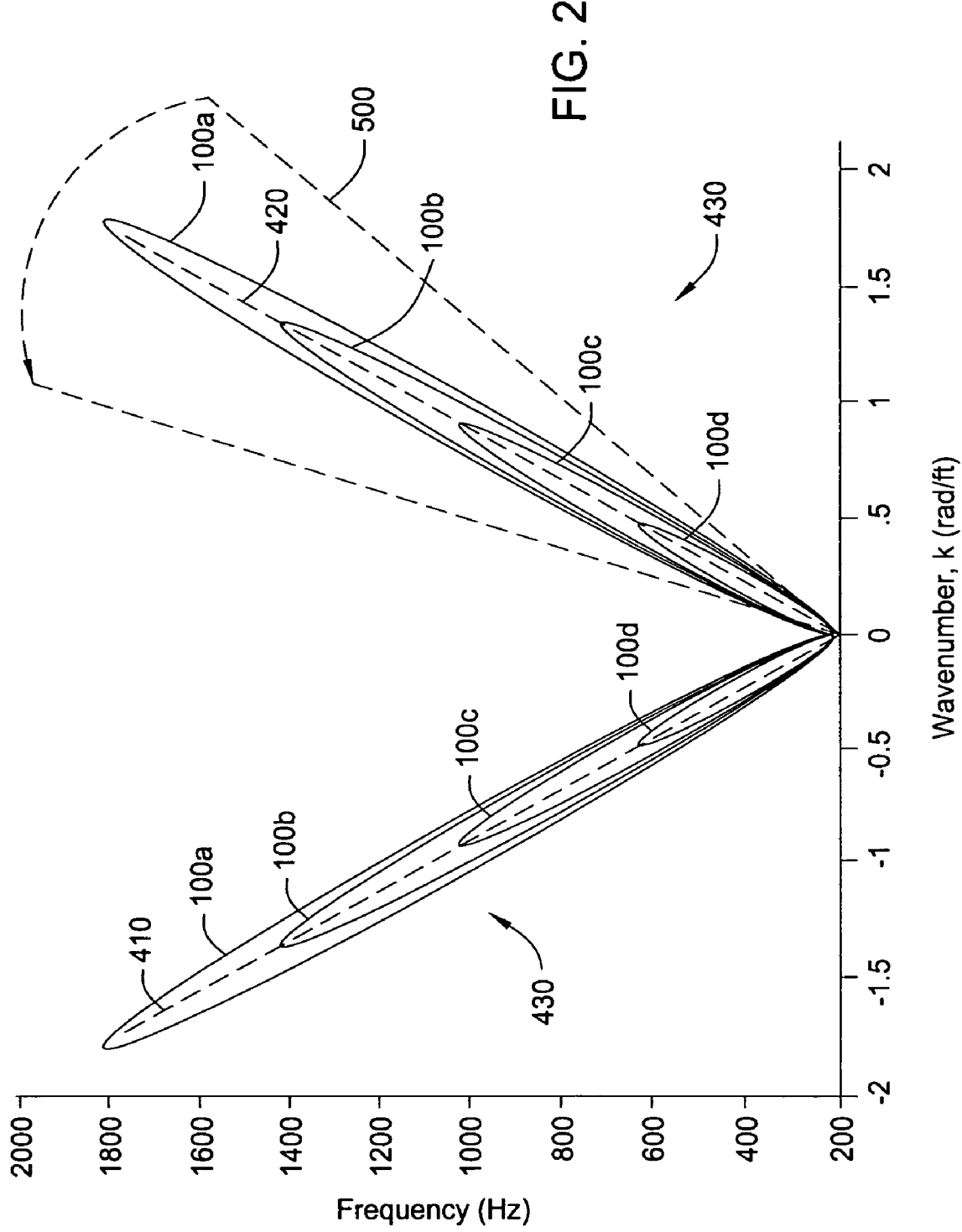
FIG. 2 illustrates a kω plot with an acoustic ridge occurring above and below the meter.

FIG. 2 illustrates an exemplary kω plot to be analyzed. The vertical axis of the plot is the temporal or angular frequency (ω) of the signal in rad/s and the horizontal axis is the spatial frequency or wave number (k) (e.g., in 1/ft). Each point (i.e., frequency) in the plot has associated with it a power level (in dB) denoted by regions 100a-100d. The kω plot constitutes a data set in which each pixel comprises a particular power value.

Accumulation of all of the acoustic events represented in the plot lie generally along straight lines, referred to as "ridges" 430. These ridges reflect the fact that all of the detected various acoustic events, each having its own unique frequency constitutions, travel through the fluid at approximately the same speed through the fluid, i.e., the fluid speed of sound. This fluid speed of sound, c, can therefore be calculated by computing a best fit line(s) 410, 420 within the ridge(s), and determining that line's slope, where ω=ck.

Power of the various acoustic phenomena that are represented in the kω plot can be determined. Accordingly, regions 100a-100d represent areas of differing power levels with region 100d representing the highest power levels (e.g., 20 db), region 100c representing lower power levels (e.g., 10 db), etc. The power regions are more uneven or blotchy in shape than the idealized representation of the power levels depicted in the figures herein.

The kω plot allows for directionality of the acoustical disturbances to be determined. Referring to FIG. 1, the measured acoustics arrive at the sensor array 110 as either left traveling waves or right traveling waves corresponding respectively to energy on the left side or the right side of the kω plot. Because the speed of the fluid flowing within the pipe is usually much smaller than the speed of sound in the fluid, these left traveling or right traveling acoustic disturbances approach the array 110 at approximately the same speed (assuming that the Mach number of the flow is <<1). Left traveling disturbances correspond to negative k values while right traveling disturbances correspond to positive k values. Thus, the kω plot exhibits two ridges 430 since acoustics are generated from both the left and the right of the array 110. A first ridge along line 410 is indicative of left traveling acoustics, and a second ridge along line 420 is indicative of right traveling acoustics. Because the left traveling and right traveling waves arrive at approximately the same speed, the absolute value of the slopes of both lines 410, 420 is approximately equal and indicative of the speed of sound in the fluid.

The ridges 430 in the kω plot are assessed in the system by a computerized ridge identifier 27, as shown in FIG. 1, which can identify the ridges 430 using computerized techniques for assessing plots or plot data files. For example, the ridge identifier 27 can be preprogrammed with a power level threshold in which pixels in the plot having values exceeding this threshold are deemed to constitute a portion of the ridge 430. Once the area of the plot containing the ridge 430 has been identified, its slope (i.e., lines 410 and 420) can be determined by analyzer 28, which preferably employs a weighted least squares fitting algorithm or other fitting algorithm.

Referring still to FIG. 1, the sensors 14, 16, 18 have suitable spacing (preferably, equally spaced by ΔX) to detect acoustical frequencies selected of interest. If a single frequency component is considered, the disclosed system obtains information about the wavelength λ (or the wave number k) of that frequency component essentially by sensing the phase of that component at (at least) any two of the sensors 14, 16, 18. Thus, the separation ΔX can be determined to be a particular fraction of a wavelength of the sound to be measured. The information is only unambiguous if the sensors sample frequently enough to avoid temporal aliasing and are close enough to avoid spatial aliasing. For example, the system may incorrectly indicate a value for the wavelength that is twice the actual value if the sensors are a distance ΔX apart that is two wavelengths of the frequency component being measured. Additional sensors spaced at appropriate intervals can be added should it be necessary to resolve frequencies over a larger range than a single spacing distance permits.

The presence of sand attenuates power of the acoustics in the fluid. Additionally sand alters the speed of sound in the fluid such that decreasing speed of sound measurements correspond to increasing sand concentrations. Accordingly, assessing these effects on power and/or the speed of sound in the fluid can infer the presence of sand. Moreover, this detection using the sensor array 110 disclosed herein can be performed continuously and directly at the production pipe before sand reaches the top of the well.

Attenuation of acoustics detected with the sensor array 110 indicates presence of sand with increasing attenuation corresponding to rising sand concentrations. Qualitative detection of sand can be made by detection of attenuation from a base signal where no sand is present. Additionally, quantitative detection of sand can be accomplished by calibrating the amount of attenuation with the concentration of sand. The attenuation due to sand occurs in frequency ranges above about 5 kHz. Accordingly, the sensors and/or the processing equipment can collectively analyze frequency ranges of, for example, from 5 kHz to 20 kHz or from 5 kHz to 15 kHz.

With reference to the kω plot shown in FIG. 2, the attenuation may be visually observed by diminished power indicated by diminution of regions 100a-100d to respectively lower power levels. A further visual distinction may be present based on a change in a ratio of amplitude of the first ridge along line 410 to amplitude of the second ridge along line 420, as described further below regarding the Example. Appropriate algorithms of the analyzer 28 can automate the detection of sand based on this observed attenuation within the kω plot.

Processing based on kω plots may apply temporal and spatial filtering techniques to increase the effective signal-to-noise ratio, i.e., the disclosed method may only consider the attenuation of acoustics over a specific frequency range. Other signals of the sensor output such as electrical noise, vortical noise, impact noise propagating within the production tubing may all be effectively filtered out by the disclosed method.

EXAMPLE

Figure 3:
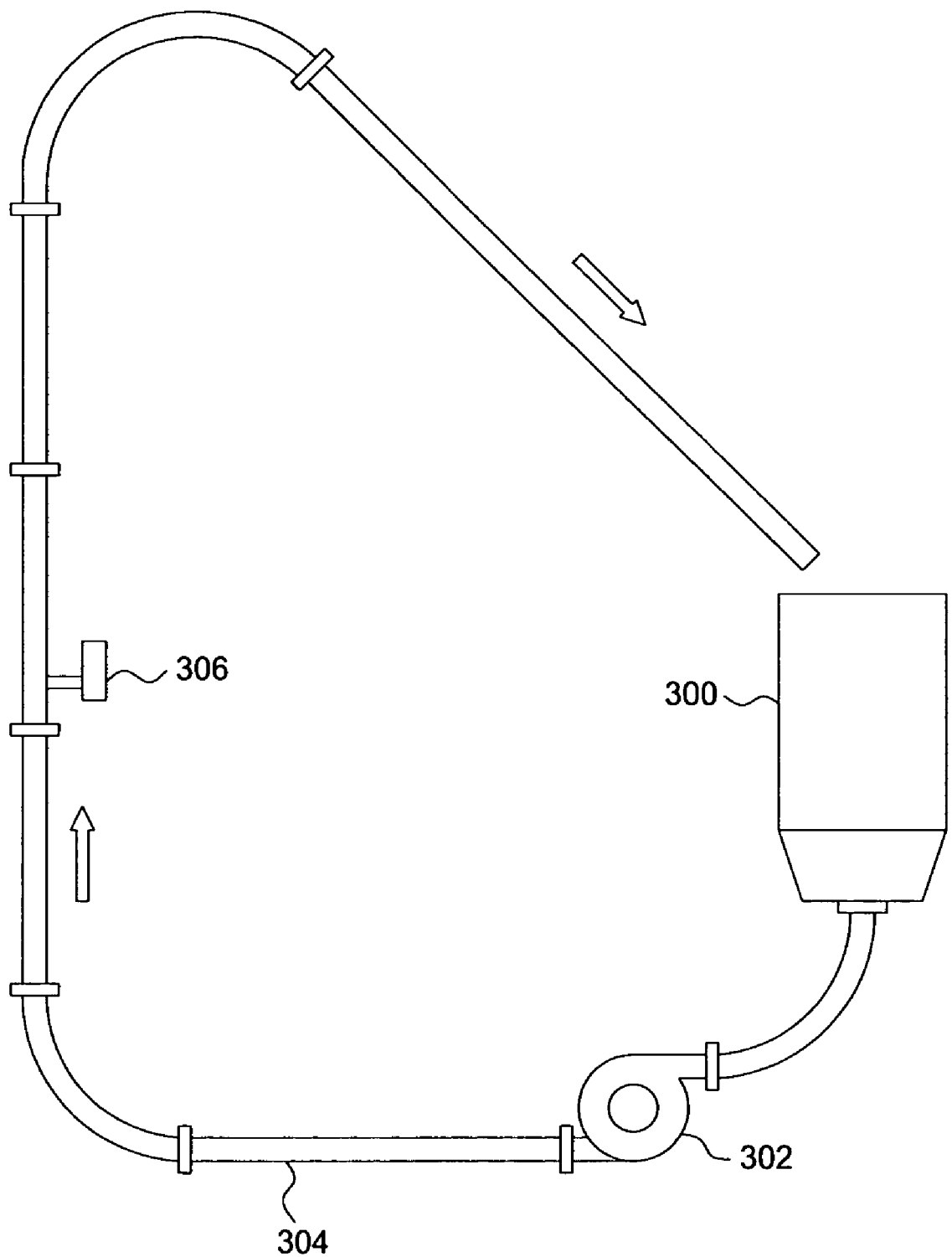
FIG. 3 illustrates an experimental flow loop setup used in experiments which demonstrated ability to detect sand flowing in a fluid.

FIG. 3 illustrates an experimental setup that has been used to demonstrate the ability to detect sand flowing in a fluid as disclosed herein. The setup provides a water loop that includes a reservoir 300, a pump 302, a conduit 304 and a sensor array 306 such as shown in FIG. 1. In operation, the pump 302 urged water from the reservoir 300 upward through the conduit 304 and sensor array 306 in the experiment described herein, prior to the water being returned to the reservoir 300. The pump was operated to provide a flow rate of 550.0 gallons per minute (gpm) corresponding to a 26.0 feet per second flow velocity. Sand particles introduced into the water flow were crystalline silica with a mean diameter of 180.0 micron and a specific gravity of 2.65. The volume and mass percentages of the sand used in the experiments are shown in Table 1.

TABLE 1

| Experiment | Mass percentage of sand | Volume of sand |
|---|---|---|
| 0 | 0 | 0 |
| 1 | 1.5 | 0.57 |
| 2 | 3 | 1.14 |

Figure 4:
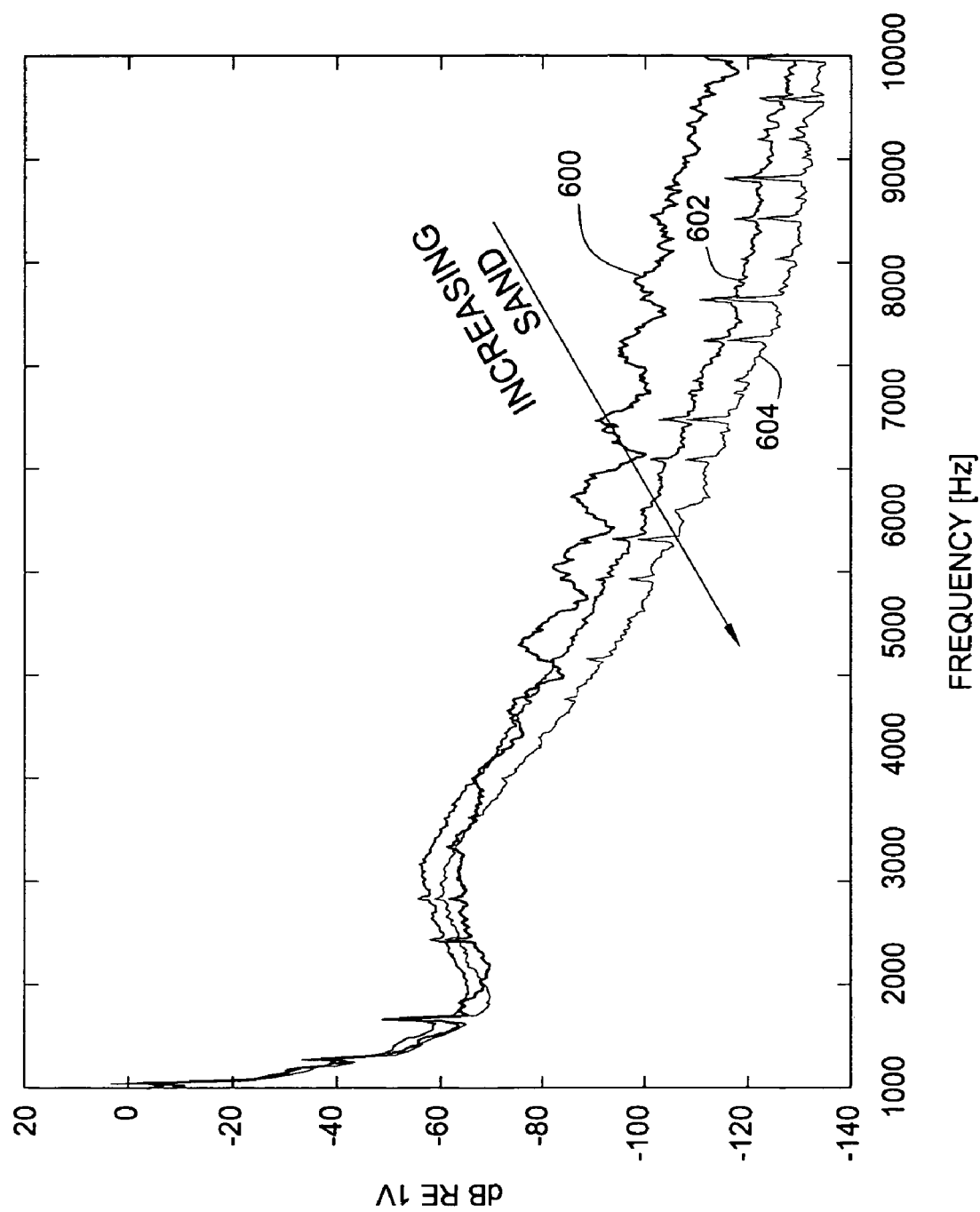
FIG. 4 illustrates an acoustic spectra plot generated based on the experiments.

FIG. 4 illustrates an acoustic spectra plot for frequencies from 1.0 kHz to 10.0 kHz. Curve 600 represents a baseline recorded during Experiment 0 (no sand). Comparatively, curve 602 identifies the signals generated during Experiment 1 (1.5% mass sand) while curve 604 identifies the signal produced via Experiment 2 (3% mass sand).

Figure 5:
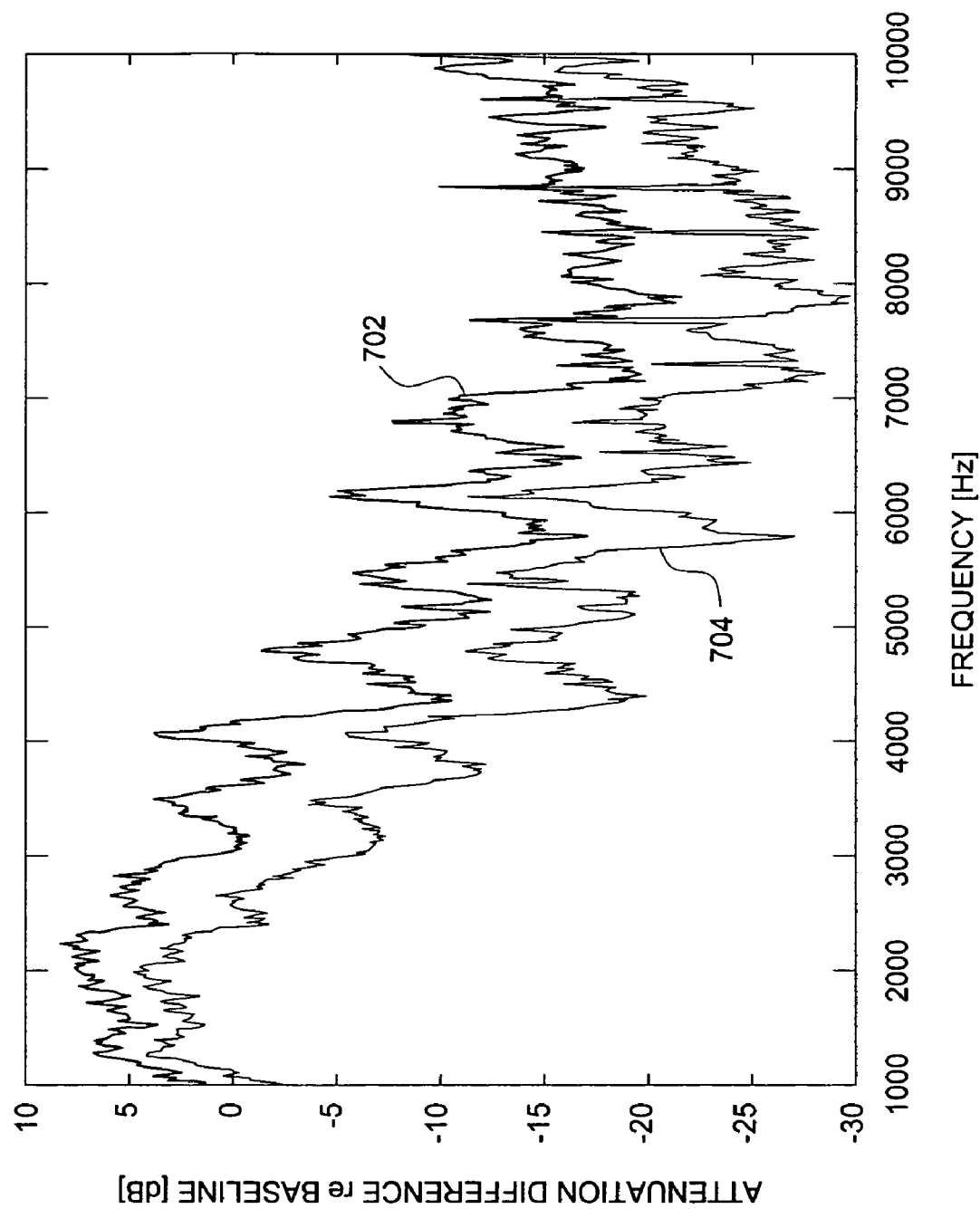
FIG. 5 illustrates an attenuation plot based on the detected signals shown in the spectra plot in FIG. 4.

FIG. 5 shows an attenuation plot based on the detected signals shown in the spectra plot in FIG. 4. Line 702 represents the difference between spectral levels of Experiment 0 and Experiment 1. Similarly, line 704 represents the difference between spectral levels of the baseline with no sand and the higher 3% mass sand. The addition of sand provided substantially no attenuation of acoustic signals below 3.0 kHz, as evidenced by the difference being positive. However, sand introduced into the flow attenuated all signals from Experiments 1 and 2 in the spectra above 5.0 kHz.

Figure 6:
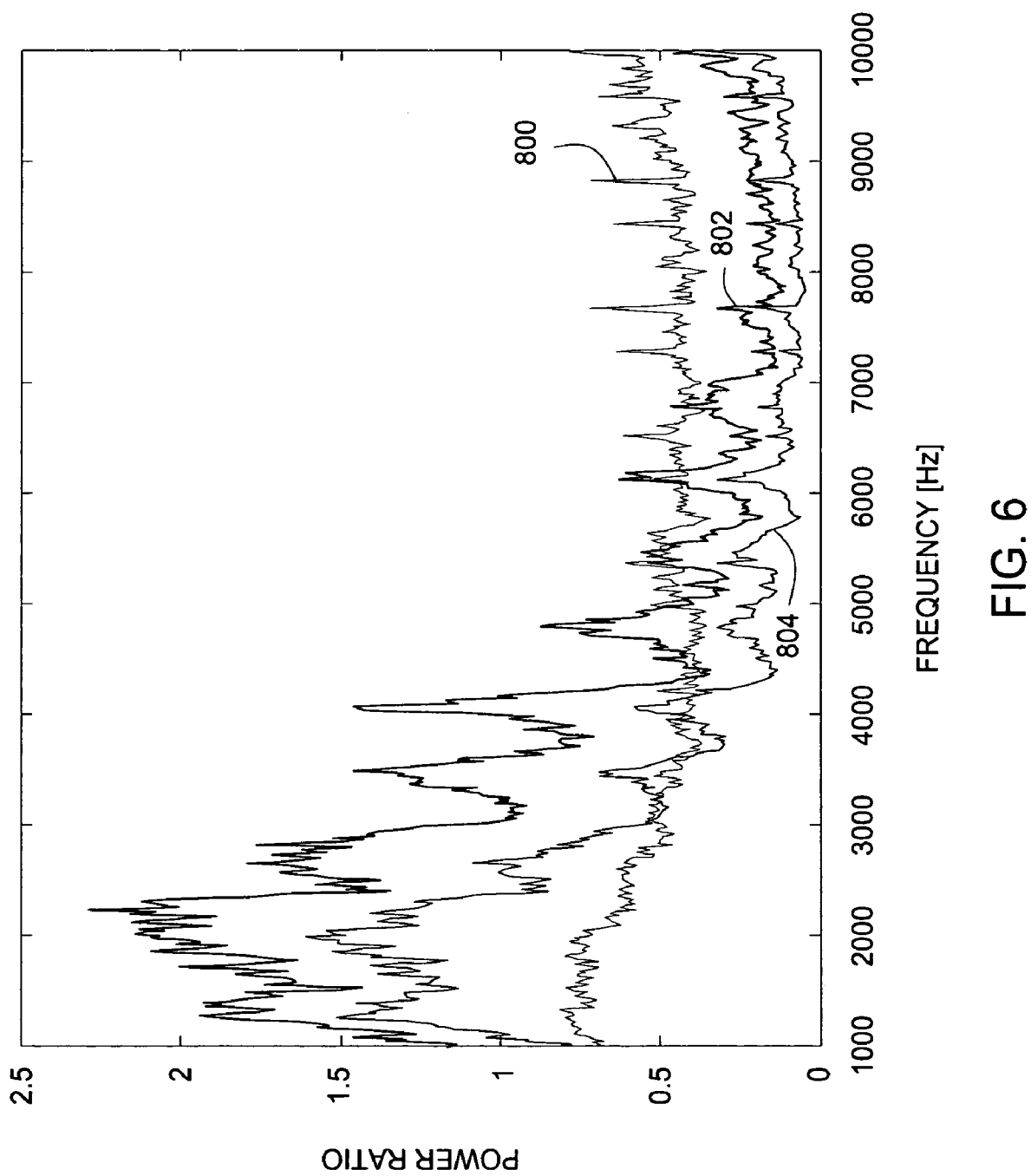
FIG. 6 illustrates a power ratio plot comparing the experiments.

FIG. 6 illustrates a power ratio plot of Experiments 1 and 2 to Experiment 0, as well as Experiment 2 to Experiment 1. The power ratio is lower for the higher mass loading of sand, as illustrated by line 800 corresponding to the power ratio of Experiment 2 to Experiment 1. For the line 800 and both line 802 corresponding to the power ratio of Experiment 1 to Experiment 0 and line 803 relating to the power ratio of Experiment 2 to Experiment 0, the power ratios are substantially constant and all lower than one above 5.0 kHz.

Figure 7:
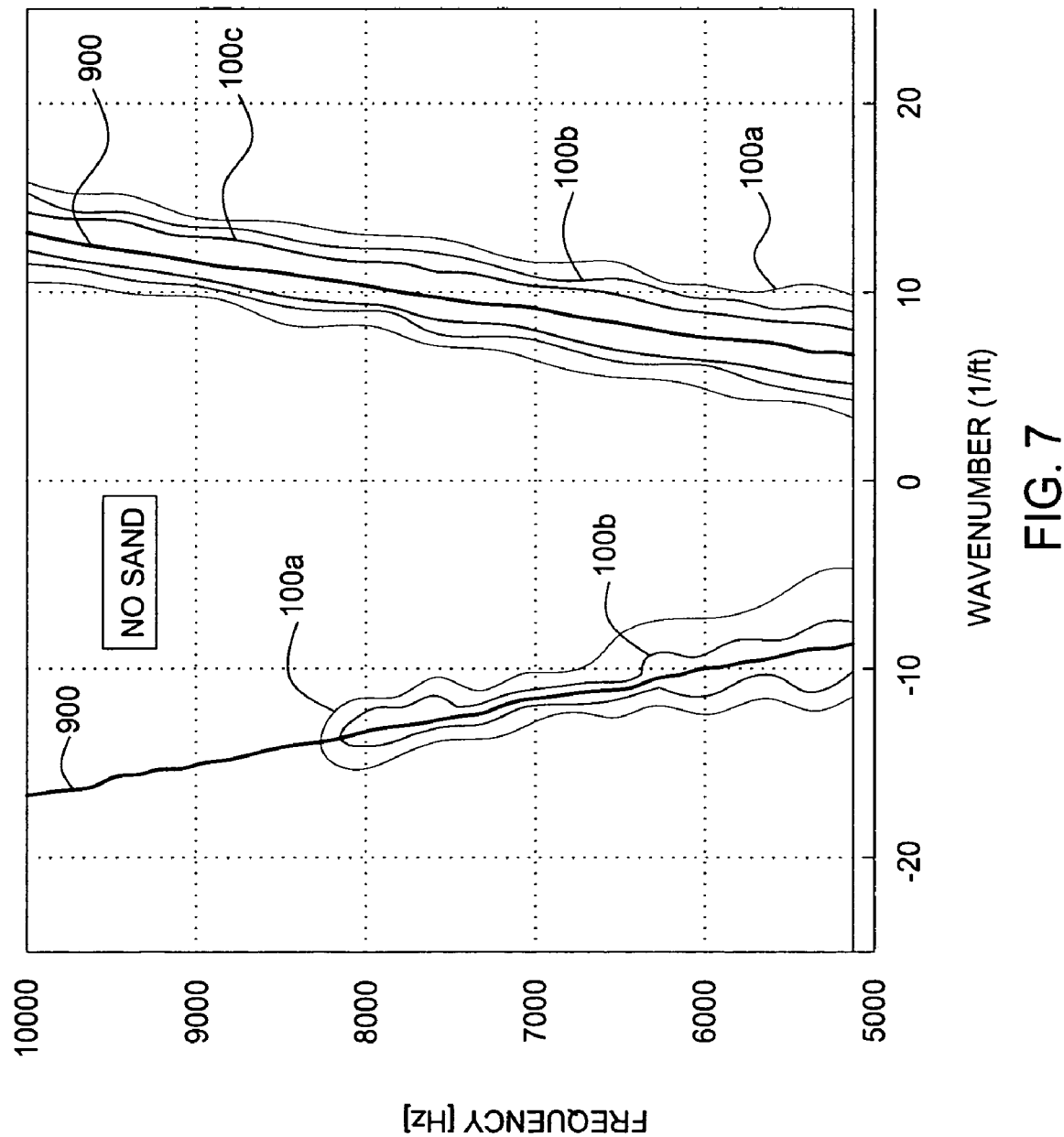
FIGS. 7-9 show schematically kω plots generated by the experiments without sound, with 1.5% sand mass and with 3% sand mass, respectively.
Figure 8:
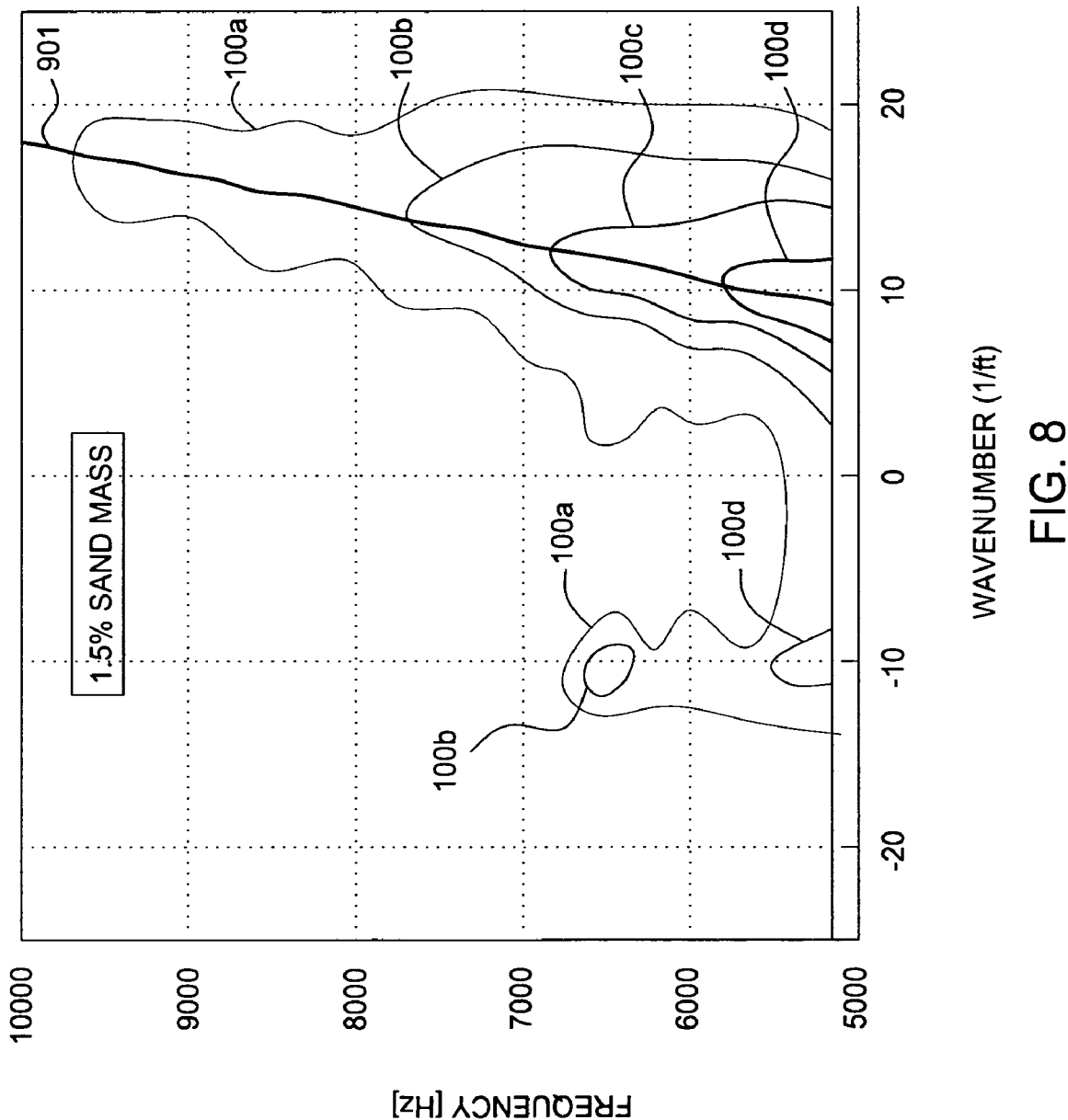
Figure 9:
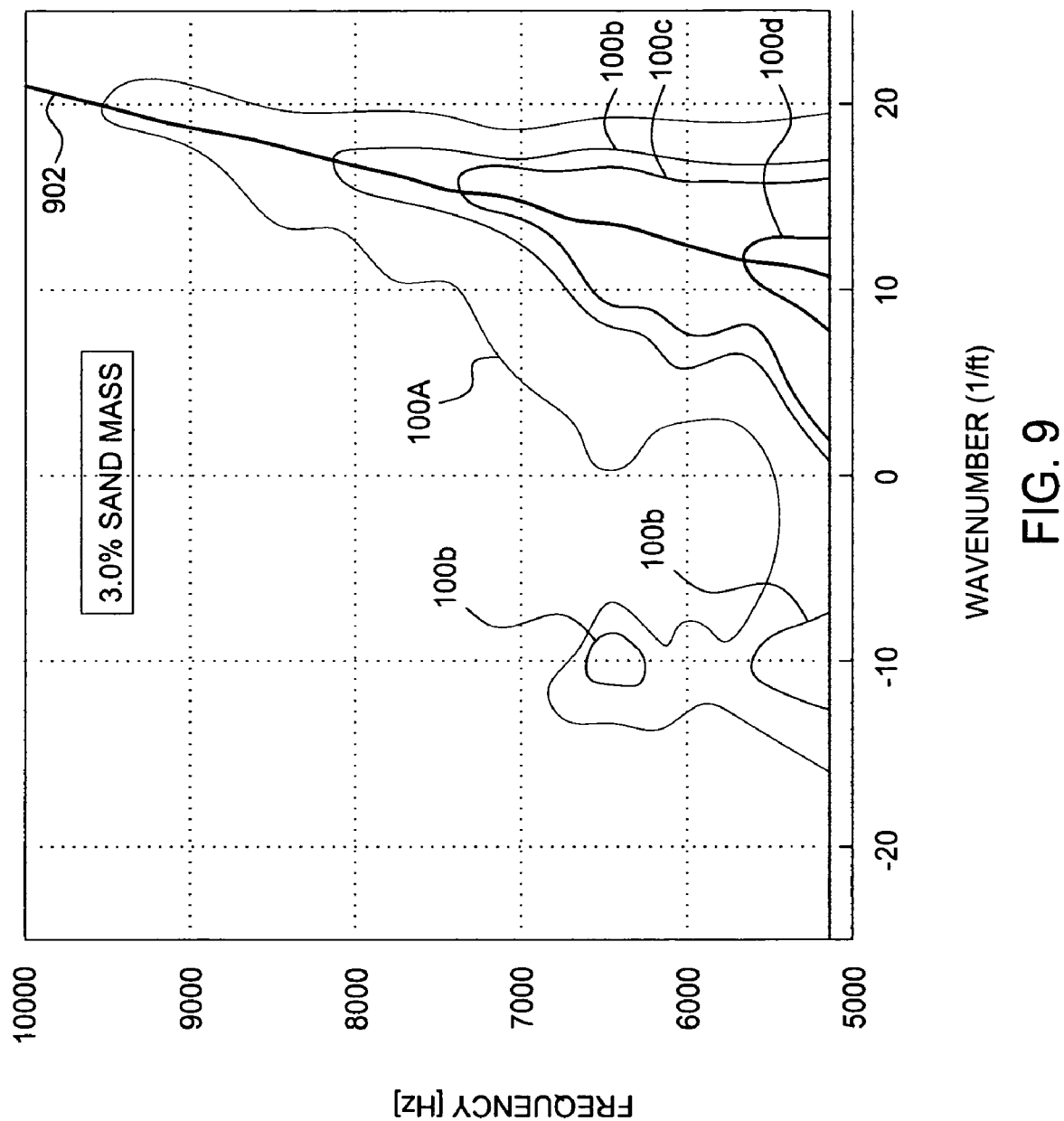

FIGS. 7-9 show schematically kω plots generated by the experiments without sand, with 1.5% sand mass and with 3% sand mass, respectively. Contour nomenclature as used in FIG. 2 is maintained in these plots. These plots evidence that the acoustics diminished and acoustic signatures were altered with the addition of sand. For example, attenuation caused by the addition of sand changed a ratio of amplitude of the left side of the kω plots to amplitude of the right side of the kω plots. The left side of the kω plots indicate acoustic waves reaching the sensor array 306 traveling from bottom to top while the right side of the kω plots indicate acoustic waves reaching the sensor array 306 traveling from top to bottom.

Higher amplitude of the power on the right side of the kω plot in FIG. 7 indicates higher acoustic are generated above the sensor array 306. Weaker amplitude of the power on the left side of the plot resulted from acoustics originating above the sensor array returning after being reflected below the sensor array 306. These reflected acoustics were weaker due to traveling a longer distance through the fluid even though no sand was present. Since sand in the water further attenuates the acoustics in terms of decibels per unit distance, addition of sand disproportionately diminished the acoustics from below the sensor corresponding to the left side of the plot. Consequently, the ratio of amplitude of the right side of the plot to amplitude of the left side of the plot is changed between each of FIGS. 7-9. For some embodiments, the acoustic being monitored may have an originating source below the sensor array 306, which results in higher amplitude of the power on the left side of the kω plot and also inverts the ratio without otherwise altering the analysis.

Lines 900, 901 and 902 in FIGS. 7-9 identify a best fit of the data therein such that the slopes of the lines represent the speed of sound in the fluid. From the slope of the lines 900,

901 and 902, the speed of sound in Experiments 0 through 2 was calculated at 2500 feet per second (ft/sec), 2450 ft/sec and 2350 ft/sec, respectively. The sound speed in water without entrained gas as measured with this technology is approximately 4650 ft/sec. Accordingly, Experiment 0 that did not have any sand provided a relatively lower sound speed due to entrained gas of about 200.0 part per million (ppm).

Theoretical acoustic models for particle suspensions, predict that sand detection is not possible in multiphase mixtures such as liquid and gas mixtures. These theoretical models predict a strong sensitivity to gas but not solid particles. While not predicted by the conventional models, trends revealed by the experiments described herein indicated that sand can be detected even in the presence of gas. The theoretical models describe a distorted acoustic signature due to sand suspended in a flowing mixture and attenuation and dispersion due to viscous dissipation, non-viscous inertial, and multiple scattering effects. The results of the experiments showed significant changes in attenuation that were not predicted.

Attenuation due to sand loading based on theoretical calculations using the models is expected to be approximately 0.008 decibels (dB) and 0.016 dB for the 1.5% and 3% sand mass experiments, respectively. However, attenuation due to increase in gas volume fraction (GVF) based on theoretical calculations is expected to be relatively much higher than attenuation due to sand loading at frequency ranges above 5 kHz. In other words, the attenuation due to increase in GVF is expected to be more than two orders of magnitude higher than the theoretical attenuation levels due to sand. Consequently, it was believed that even miniscule amounts of gas would cause large decreases in the speed of sound and dominate the attenuation effects.

The experiments further illustrate the results not being predicted by hypothetically treating the observed change in speed of sound as only being due to an increase in gas bubbles in the water. Using this hypothetical assumption, the GVF values for Experiments 1 and 2 are 216.0 ppm and 244.0 ppm, respectively. Relative attenuation between the GVF of 200.0 ppm and these higher GVF values of 216.0 ppm or 244.0 ppm is expected to be only on the order of less than about 1.0 or 2.0 dB, respectively, for frequencies less than 10 kHz. Therefore, this relative attenuation due to any possible variation of GVF does not account for the attenuation levels seen in FIG. 5, which is on the order of 20 dB.

For some embodiments, apparatus and methods as disclosed herein can detect particulates in any pipe and in other industrial environments even though the foregoing describes detection of sand within a production pipe of an oil/gas well. While the foregoing is directed to embodiments of the present invention, other and further embodiments of the invention may be devised without departing from the basic scope thereof, and the scope thereof is determined by the claims that follow.

What is claimed is:

1. A method of detecting particles in a fluid within a conduit, comprising:
    measuring acoustic disturbances within the fluid with at least two pressure sensors in order to produce a pressure signal data set; and
    monitoring the data set to detect a change relative to a control set, wherein the change indicates that particles are present in the fluid and the change comprises the reduction in power of the acoustic disturbances determined by a variation relative to the control set in a ratio of amplitude in acoustic waves traveling in a first direction to amplitude of acoustic waves traveling oppositely in a second direction.

2. The method of claim 1, wherein the change in the data set comprises the reduction in power of acoustic disturbances above 5 kHz.

3. The method of claim 1, wherein the change in the data set comprises the reduction in power of acoustic disturbances between 5 kHz and 20 kHz.

4. The method of claim 1, wherein the change in the data set comprises the reduction in power of acoustic disturbances that is greater than 5.0 decibels between 5 kHz and 20 kHz.

5. The method of claim 1, wherein the fluid is flowing within the conduit while measuring the acoustic disturbances.

6. A system for detecting particles in a fluid within a conduit, comprising:
    at least two sensors disposed along the conduit, the sensors for detecting acoustic disturbances within the fluid;
    a processor for converting pressure signals from the at least two sensors into a data set indicative of power of the acoustic disturbances;
    an analyzer for assessing the data set and determining whether the power of the acoustic disturbances is attenuated relative to a control set; and
    an output to indicate presence of particles in the fluid when the data set is attenuated relative to the control set.

7. The system of claim 6, wherein the analyzer compares the data set and the control set at frequencies above 5 kHz and the output is configured to indicate that particles are present when the data set is attenuated more than a preset value.

8. The system of claim 6, wherein the analyzer compares the data set and the control set at frequencies within a range of 5 kHz to 20 kHz and the output is configured to indicate that particles are present when the data set is attenuated more than 5.0 decibels.

9. The system of claim 6, wherein the sensors are optically based.

10. The system of claim 6, wherein the sensors comprise polyvinylidene fluoride.

11. The system of claim 6, wherein the control set is based on substantially no particles in the fluid.

12. The system of claim 6, wherein the control set is based on a known amount of particles in the fluid.

13. The system of claim 6, wherein the analyzer is configured to monitor the data set for a change in a ratio of amplitude in acoustic waves traveling in a first direction to amplitude of acoustic waves traveling oppositely in a second direction.

14. A method of detecting particles in a fluid within a conduit, comprising:
    measuring acoustic disturbances within the fluid with at least two pressure sensors to produce pressure signals;
    converting the pressure signals to provide a data set indicative of power of the acoustic disturbances;
    assessing the data set and determining whether the power of the acoustic disturbances is attenuated relative to a control set; and
    determining if particles are in the fluid based on whether the data set is attenuated relative to the control set indicating that particles are present.

15. The method of claim 14, wherein the fluid is flowing within the conduit while measuring the acoustic disturbances.

16. The method of claim 14, wherein the fluid comprises a liquid with entrained gas.

17. The method of claim 14, wherein assessing the data set comprises comparing the data set and the control set at frequencies above 5 kHz to determine whether the data set is attenuated.

18. The method of claim 14, wherein assessing the data set comprises comparing the data set and the control set at frequencies within a range of 5 kHz to 20 kHz to determine whether the data set is attenuated.

19. The method of claim 14, wherein assessing the data set includes monitoring for a change in a ratio of amplitude in acoustic waves traveling in a first direction to amplitude of acoustic waves traveling oppositely in a second direction.

20. The method of claim 14, further comprising adjusting a production parameter of a well upon determining that particles are present in the fluid.

* * * * *